United States Patent [19]

Oppelt

[11] Patent Number: 4,905,675

[45] Date of Patent: Mar. 6, 1990

[54] SHOCK WAVE GENERATOR FOR AN EXTRACORPOREAL LITHOTRIPSY DEVICE

[75] Inventor: Sylvester Oppelt, Bamberg, Fed. Rep. of Germany

[73] Assignee: Siemens Aktiengesellschaft, Berlin and Munich, Fed. Rep. of Germany

[21] Appl. No.: 182,297

[22] Filed: Apr. 15, 1988

[30] Foreign Application Priority Data

Apr. 27, 1987 [DE] Fed. Rep. of Germany ... 8706039[U]

[51] Int. Cl.$^4$ .............................................. A61B 17/22

[52] U.S. Cl. .................................................. 128/24 A

[58] Field of Search ................. 128/24 A, 328, 660.03

[56] References Cited

U.S. PATENT DOCUMENTS 4,539,989 9/1985 Forssmann et al. ................ 128/328

4,669,472 6/1987 Eisenmenger ....................... 128/328

4,793,329 12/1988 Mahler et al. .................... 128/24 A 4,794,914 1/1989 Mahler et al. .................... 128/24 A

FOREIGN PATENT DOCUMENTS 3505894 8/1986 Fed. Rep. of Germany ...... 128/328

1532008 11/1978 United Kingdom .

*Primary Examiner*—Ruth S. Smith

*Assistant Examiner*—John D. Zele

*Attorney, Agent, or Firm*—Hill, Van Santen, Steadman & Simpson

[57] ABSTRACT

A shock wave generator suitable for use in an extracorporeal lithotripsy device to disintegrate calculi in a life form in vivo has a flat coil connectable to a high voltage supply, a membrane assembly disposed opposite the coil and a housing, closed on one side by the membrane, filled with a shock wave transmissive fluid. The membrane assembly has a carrier plate of electrically insulating material, and an electrically conductive section applied at one side of the carrier. The membrane assembly is connected to the housing at its edge. The material of the carrier is insensitive to cavitation, and the carrier is elastically yielding at least in the region of its edge. The electrically conductive section is electrically insulated from the terminals of the coil, and the membrane assembly is attached to the housing so that the electrically conductive section faces the flat coil.

9 Claims, 3 Drawing Sheets

SHOCK WAVE GENERATOR FOR AN EXTRACORPOREAL LITHOTRIPSY DEVICE

BACKGROUND OF THE INVENTION

1. Field of the Invention

The present invention is directed to a shock wave generator for use in an extracorporeal lithotripsy unit.

2. Description of the Prior Art

Shock wave generators are known in the art, for example as described in German OS 33 12 104, having a flat coil connectable to a high voltage supply and disposed opposite a membrane which closes a housing filled with a shock wave transmissive fluid, such as water. The membrane has a carrier plate consisting of an electrically insulating material, and has an electrically conductive section disposed on one side of the carrier. The membrane is connected to the housing at its edge, with the electrically conductive section being insulated from the windings of the flat coil.

The high voltage supply for shock wave generators of this type includes a capacitor chargeable to several kilovolts, for example 20 kV. The energy stored in the capacitor is rapidly discharged into the coil, so that the coil generates a magnetic field extremely rapidly. At the same time, a current is induced in the electrically conductive section of the membrane. This current being opposite to the current flowing in the coil, and consequently generating an opposing magnetic field. The interaction of the two magnetic fields causes the electrically conductive section of the membrane and the carrier plate connected thereto to be rapidly repelled from the coil. This movement generates a shock wave in the fluid-filling housing, which is focused in a known manner to the calculi, for example, kidney stones, in the body of a life form, and effects disintegration thereof.

The membrane in conventional shock wave generators of this type is secured to the housing by rigidly clamping the edge of the carrier. When the membrane is driven to generate a shock wave, the membrane is thus exposed to sudden bending stresses which can result in over-stressing of the membrane, and ultimately in failure thereof. To alleviate these effects, the electrically conductive section of the membrane in conventional shock wave generators is annular. This results in a reduced mechanical stressing of the electrically conductive section of the membrane, however, the carrier of the membrane is still exposed to considerable stresses, so that the risk of rupture is particularly high at the edge of the carrier, because of the rigid clamping at that location.

To achieve an optimal conversion of the electrical energy generated by the high voltage supply into impact energy, it is necessary in conventional shock wave generators to attach the electrically conductive section of the membrane as close as possible to the flat coil. Such placement is subject to limitations, however, because a certain insulating distance must be maintained to avoid voltage arcing between the membrane and the coil. For this purpose, an insulating foil is sometimes interposed between the membrane and the coil. Voltage arcing deteriorates the effectiveness of the shock wave generator, and additionally can lead to damage of the membrane, thereby diminishing the useful life of the unit.

It is standard in conventional shock wave generators to connect the electrically conductive section of the membrane to ground potential together with one terminal of the coil. This standard practice requires such a large distance to be present between the electrically conductive section of the membrane and the flat coil in such conventional shock wave generators that an unsatisfactory efficiency in the conversion of electrical energy into impact energy results.

In such conventional shock wave generators, a cavitation problem also exists as a consequence of the relatively high speed of the membrane within the fluid which occurs during the generation of shock waves. Such cavitation can cause pitting of the membrane, thus contributing to its premature failure.

SUMMARY OF THE INVENTION

It is an object of the present invention to provide a shock wave generator of the type described above wherein damage to the membrane due to excessive mechanical stresses, voltage arcing between the membrane and the flat coil, and cavitation of the membrane is avoided, so that the membrane has a long useful life without a significant degrading influence on the efficiency of the conversion of electrical energy into impact energy.

The above object is achieved in a shock wave generator constructed in accordance with the principles of the present invention having a carrier having a central region consisting of material insensitive to cavitation, and the carrier having an elastically yielding section at least in the region of its edge. The electrically conductive section is electrically insulated from the terminals of the flat coil, and the membrane is attached to the housing with the electrically conductive section facing the flat coil.

As a result of the yielding section of the carrier in the region of its edge, the membrane as a whole can move in the direction of the force or forces acting on the membrane when shock waves are generated. Deformations of the membrane stemming from the nature of the fastening of the membrane to the housing, ad the excessive mechanical stresses associated therewith, are thus avoided. The membrane therefore exhibits an enhanced service life compared to membranes in conventional shock wave generators. Moreover, the shock wave generated in a shock wave generator constructed in accordance with the principles of the present invention can be better focused, because deviations in the shape and pressure distribution of the impact front from an ideal front, caused by deformations of the membrane, are avoided due to the central region going resistant to the effects of cavitation.

A further increase in the useful life of the membrane is achieved by insulating the electrically conductive section of the membrane from the terminals of the flat coil. In conventional shock wave generators, wherein the electrically conductive section is at the same potential as one of the terminals of the flat coil, the insulating distance between the flat coil and the electrically conductive section corresponds to the physical distance between the flat coil and the membrane. In the shock wave generator disclosed herein, wherein the electrically conductive section is electrically insulated from the terminals of the flat coil, the insulating distance corresponds to twice the physical distance between the membrane and the flat coil, so that the risk of voltage arcing, and thus the risk of damage to the membrane, is considerably reduced.

Additionally, electrically insulating the conductive section of the membrane from the terminals of the flat coil permits the membrane to be disposed closer to the flat coil than in conventional devices while maintaining the same protection against voltage arcing as is present in such conventional devices. This permits the efficiency in the conversion of electrical energy into impact energy to be enhanced in a shock wave generator constructed in accordance with the principles of the present invention.

As a consequence of the material of the carrier in the shock wave generator constructed in accordance with the principles of the present invention being insensitive to cavitation, and the membrane being attached to the housing so that the electrically conductive section faces toward the flat coil, only that side of the carrier facing away from the electrically conductive section is in contact with the shock wave transmissive fluid. This considerably reduces the risk that the membrane will prematurely fail as a consequence of pitting caused by cavitation.

In one embodiment of the invention, the carrier consists of an elastomer material, such as rubber. Such material is a good insulator, and is insensitive to cavitation as a result of its elastic resilience. Moreover, the desired elastic resilience of the carrier at the region of its edge can be achieved using such material under certain conditions without undertaking additional measures. In the most simple case, the carrier can be a plate which is elastically resilient over its entirety, having a thickness selected so that the carrier exhibits the desired resiliency at its edge. The lack of rigidity of such a carrier can be compensated by using a sufficiently rigid electrically conductive section.

If the electrically conductive section is not needed or desired to increase the rigidity of the membrane, the electrically conductive section in one embodiment of the invention may be formed by a metal foil, for example, aluminum. Such a membrane can be manufactured in a simple manner by attaching a metal foil corresponding to the shape of the electrically conductive section to the membrane by gluing or vulcanization.

In a further embodiment of the invention, the electrically conductive section may be electrically insulated from the housing in addition to being electrically insulated from the terminals of the flat coil. This is of particular significance if the housing is at a common potential, for example ground potential, with one of the terminals of the flat coil. In such a generator, insulating the electrically conductive section from the terminals of the coil would be ineffective if the electrically conductive section were not also electrically insulated from the housing.

In another embodiment of the invention, the membrane of the shock wave generator may consist of a plurality of electrically conductive section, for example, a plurality of concentric rings.

In another embodiment of the invention, the volume between the membrane and the flat coil can be evacuated. An optimum seating of the membrane against the flat coil is then guaranteed which is advantageous to the energy conversion efficiency of the shock wave generator.

Figure 3:
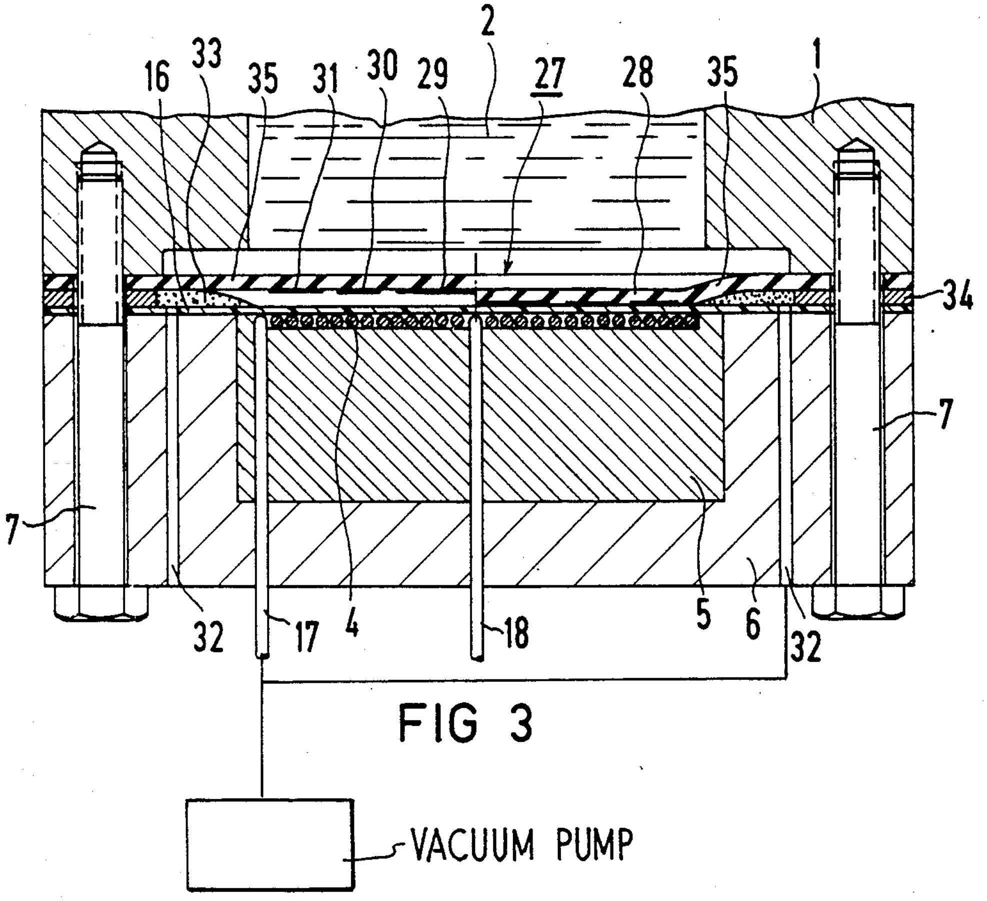
FIG. 3 is a side sectional view of a portion of a further embodiment of a shock wave generator constructed in accordance with the principles of the present invention.

Fiugre 4 is a plane view of a portion of the membrane of the shock wave generator shown in FIG. 3.

DESCRIPTION OF THE PREFERRED EMBODIMENTS

Figure 1:
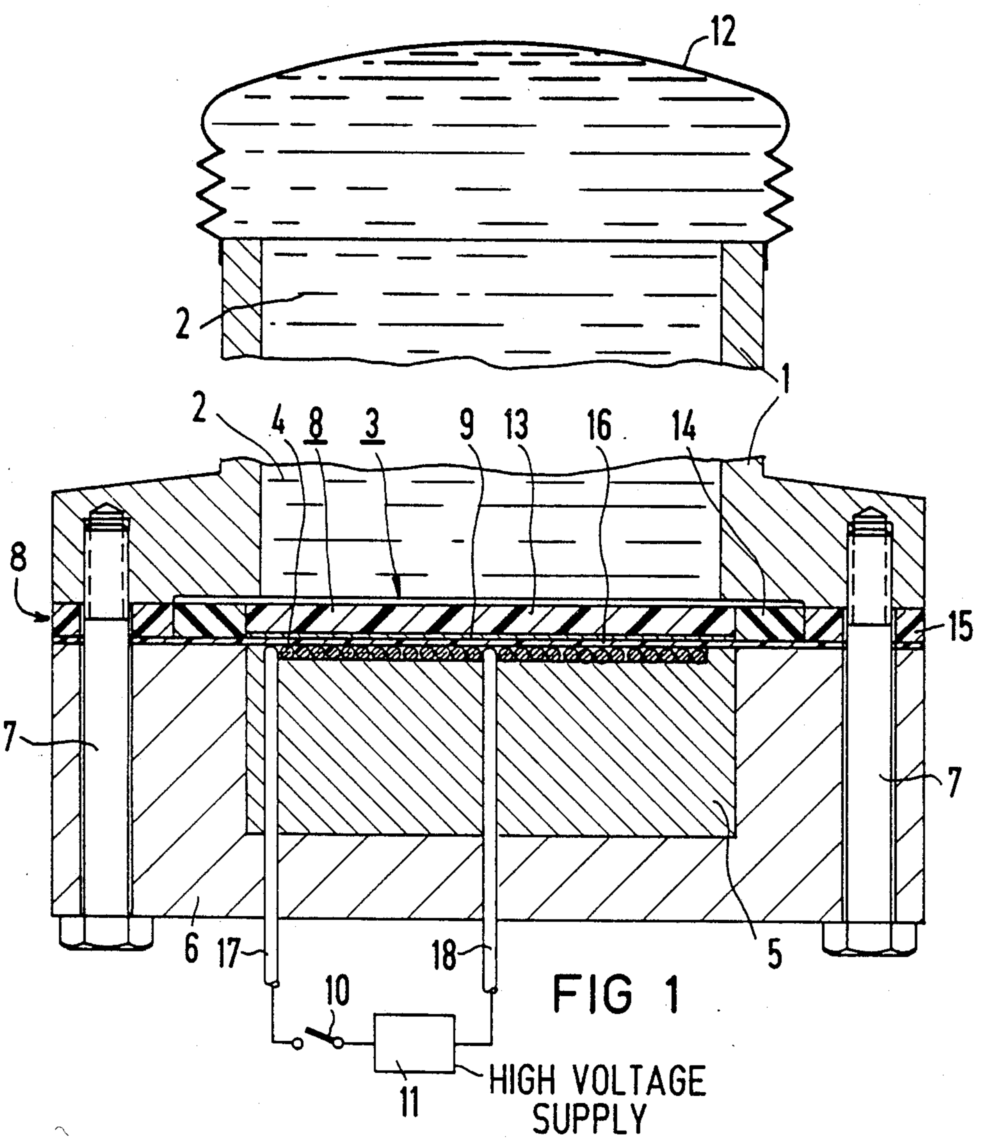
FIG. 1 is a side sectional view of the relevant components of a shock wave generator constructed in accordance with the principles of the present invention.

A shock wave generator constructed in accordance with the principles of the present invention is shown in FIG. 1. The generator includes a tubular housing 1 defining a volume 2 which is filled by fluid, and is closed by a membrane assembly 3. A spiral flat coil 4 is disposed on an insulator 5 opposite the membrane assembly 3. The coil 4 is held in place by a cover 6 secured to the housing 1 with screws 7.

The membrane assembly 3 has a carrier generally referenced 8 consisting of electrically insulating material, and having an electrically conductive section 9 on one side thereof. The electrically conductive section 9 has a circular shape and is attached to the side of the membrane 3 facing the flat coil 4. The membrane assembly 3 is also held in place within the housing 1 by the cover 6, with the edge of the carrier 8 being clamped by the screw 7.

For generating shock waves in the fluid contained within the volume 2, the coil 4 is connected to a schematically illustrated high voltage supply 11 by a switch 10. The high voltage supply 11 permits a pulse-like current surge to the flat coil 4, which generates a magnetic field as a consequence. At the same time, a current having an opposite directional sign is induced in the electrically conductive section 9, causing generation of an opposing magnetic field. The membrane assembly 3 is thus rapidly repelled from the flat coil 4, whereby a shock wave arises in the fluid in the volume 2. The shock wave is focused to a calculus to be disintegrated in a patient in a known manner which is not shown. Coupling of the generator to the body of the patient is achieved by a flexible sack 12 which closes the housing 1 at an end thereof remote from the membrane 3, and which is pressed against the body of the patient.

The carrier 8 is formed of a material, such as rubber, which is not only a good insulator but also is insensitive to cavitation. A central region 13 of the carrier 8, to which the electrically conductive section 9 is attached, may consist of a comparatively hard rubber having a hardness of about 90 Shore. The electrically conductive section 9 may be a copper disk attached to the central region 13 during vulcanization.

The edge 14 of the carrier 8, merging with the central region 13, is by contrast formed of a relatively soft rubber having a hardness of about 30 Shore. Because the edge 14 of the carrier 8 is elastically yielding in comparison to the central region 13, the central region 13 of the carrier 8 and the electrically conductive section 9 attached thereto can be subjected to excursion for generating shock waves without being exposed to injurious deformations and stresses. This leads to an increased useful life of the membrane 3, and further permits the generated shock waves to be better focused.

The edge 14 of the carrier 8 is followed (moving in a direction away from the center) by an annular section 15 which is held between the housing 1 and the cover 6.

The annular section 15 also consists of a rubber having a hardness of about 90 Shore so as to withstand the forces exerted by the screws 7 without significant deformation.

The central region 13, the edge 14, and the annular section 15 of the carrier 8, the different hardnesses of which are identified in FIG. 1 by appropriate cross-hatching, can be manufactured separately from each other and connected together during vulcanization. It is also possible to manufacture the carrier 8 as a one-piece component by injection molding using a form with a cavity which can be sub-divided by slides. The materials having respectively different hardnesses can then be introduced into the respective sections of the cavity simultaneously in a heated, viscous condition, and the slides retracted before the materials cure. The electrically conductive section 9 may be disposed within the form as an insert.

As can be seen in FIG. 1, an insulating foil 16 is disposed between the electrically conductive section 9 and the flat coil 4. Because the membrane assembly 3 is connected to the housing 1 and the cover 6 only by the electrically insulating carrier 8, the electrically conductive section 9 is thus insulated both from the housing 1 and the cover 6, as well as from the windings of the flat coil 4 and its terminals 17 and 18. This is also true if, for example, one of the terminals 17 or 18 of the coil 4 is at ground potential in common with the housing 1 and/or the cover 6. The effective insulating distance between the electrically conductive section 9 and the windings of the flat coil 4 as well as the terminals 17 and 18 thereof thus corresponds to twice the physical thickness of the insulating foil 16. The risk of voltage arcing between the electrically conductive section 9 and the coil 4 is thus extremely low, and damage due to such voltage arcing, which shortens the useful life of the membrane assembly 3, is virtually impossible.

As can also be seen in FIG. 1, the membrane assembly 3 is attached to the housing 1 so that the electrically conductive section 9 faces toward the flat coil 4. As a result, the electrically conductive section 9 is disposed as close as possible to the flat coil 4 (limited by the interposition of the insulating foil 16) so that a high efficiency in the conversion of electrical energy into impact energy results. Additionally, the side of the membrane assembly 3 which is in contact with the fluid in the volume 2 consists solely of the rubber of the carrier 8, which is insensitive to cavitation. The useful life of the membrane assembly 3 is thus further prolonged by avoiding or minimizing pitting which would otherwise occur as a result of cavitation.

Figure 2:
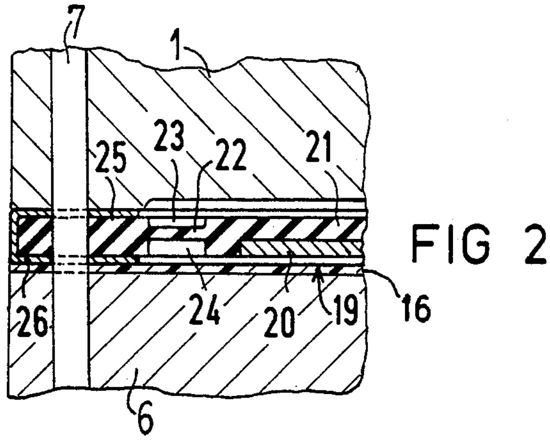
FIG. 2 is a side sectional view of a portion of a further embodiment of a membrane constructed in accordance with the principles of the present invention which may be used in the shock wave generator of FIG. 1.

Another embodiment of a membrane assembly 19 which can be used in a shock wave generator constructed in accordance with the principles of the present invention, instead of the membrane assembly 3, is shown in FIG. 2. In the membrane assembly 19 shown in FIG. 2, the electrically conductive section 20 may also be a copper disk, however in contrast to the electrically conductive section 9 discussed above, the electrically conductive section 20 has a considerably greater thickness. This is because the carrier 21 in the membrane assembly 19, as can be seen from the cross-hatching, consists of a relatively soft elastomer material having a hardness of about 40 Shore. Adequate rigidity of the membrane assembly 19 can thus only be achieved by the use of a thickened electrically conductive section 20. In order to guarantee the resiliency of the edge 22 of the carrier 21 required for the reasons discussed above, two annular recesses 23 and 24 are provided at the edge 22 of the carrier 21, so that the edge 22 has a reduced thickness. The edge 22 of the carrier 21 is followed by an annular section 25 by which the membrane assembly 19 can be held between the housing 1 and the cover 6. To give the annular section 25 the stiffness required for this purpose, the section 25 is surrounded by a sheet metal ring 26 having a U-shaped cross section, functioning as armoring.

FIGS. 3 and 4 show an embodiment of a shock wave generator constructed in accordance with the principles of the present invention differing from the embodiments described above in that the embodiment of FIGS. 3 and 4 has a membrane assembly 27 with a carrier 28 in the form of a thin elastically resilient plate consisting of elastomer material having a hardness of about 40 Shore. Three electrically conductive sections 29, 30 and 31 are disposed on the carrier 28. The sections 29, 30 and 31 consist of a thin foil, such as aluminum, secured to the carrier 28 by gluing. The conductive section 29 is a disk, whereas the electrically conductive sections 30 and 31 are rings concentrically surrounding the section 29. The conductive sections 29, 30 and 31 are suitably dimensioned so that, when driven by the flat coil 4, the sections all bend away from the flat coil 4 in a single plane. The shock wave generator in the embodiment of FIGS. 3 and 4 has all of the advantages discussed above.

Figure 4:
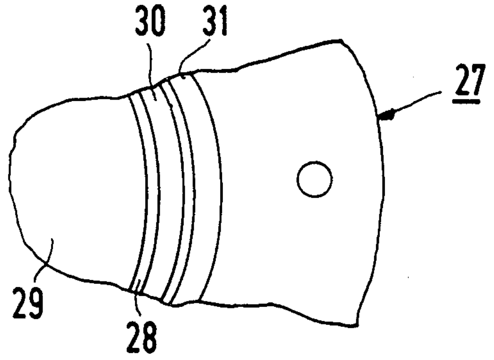

Additionally in the embodiment of FIGS. 3 and 4, the volume between the membrane assembly 27 and the flat coil 4 can be evacuated. (If the insulating foil 16 is present, as shown in FIG. 3, the relevant volume which can be evacuated is then between the insulating foil 16 and the membrane assembly 27.) For this purpose, the cover 6 is provided with a plurality of bores 32 which extend through the cover 7 and the insulating foil 16 to a porous annular section 33 of an annular element 34 which is held between the membrane assembly 27 and the insulating foil 16. The annular element 34 at its edge 35 held with the membrane and the insulating foil 16 between the cover 7 and the housing 1 with the screws 7. When the bores 32 are connected to a vacuum pump (not shown) the atmosphere between the membrane assembly 27 and the insulating foil 16 is evacuated as a consequence of the porosity of the annular section 33 so that, as shown in the right half of FIG. 3, the membrane assembly 27 rests against the insulating foil 16. The porosity of the annular section 33 permits evacuation to take place without the carrier 28 being sucked against the bores 32, which would block the bores 32 and prevent further evacuation. The electrically conductive sections 29, 30 and 31 of the membrane assembly 27 are thus located optimally close to the flat coil 4, so that a high efficiency in the conversion of electrical energy into impact energy results.

The above embodiments have been described in the context of shock wave generators wherein the windings of the flat coil are disposed in one plane, and wherein the membrane is planar. The teachings described herein, however, are equally applicable to shock wave generators having non-planar coils, such as shock wave generators wherein the windings are disposed on the surface of, for example, a calotte shell. In those shock wave generators, the membrane assembly will be correspondingly shaped.

Although modifications and changes may be suggested by those skilled in the art it is the intention of the inventor to embody within the patent warranted hereon all changes and modifications as reasonably and properly come within the scope of his contribution to the art.

I claim as my invention:

1. A shock wave generator for extracorporeal lithotripsy comprising:

a housing having a volume filled with a shock wave transmissive medium;

a membrane assembly closing one end of said volume and including a carrier disposed adjacent said volume and having a perimeter at least a portion of which is held to said housing and an electrically conductive section held to said carrier distal said volume and spaced from said perimeter, said perimeter having a substantially elastically yielding region;

a high voltage supply;

an insulating foil;

an electrically conductive coil attached to said housing and having winding arranged in a surface parallel to said membrane assembly on the side of said carrier to which said electrically conductive section is held with said insulating foil disposed between said coil and said electrically conductive section, said coil having terminals connected to said high voltage supply so that said coil generates a magnetic field in a first direction, said electrically conductive section of said membrane assembly being electrically insulated from said terminals of said coil and said windings of said coil; said coil inducing a current in said electrically conductive section of said membrane assembly to generate a magnetic field in a direction to repel said membrane assembly from said coil to generate a shock wave in said medium.

2. A shock wave generator as claimed in claim 1, wherein said carrier comprises and elastomer material.

3. A shock wave generator as claimed in claim 1, wherein said carrier comprises of rubber.

4. A shock wave generator as claimed in claim 1, wherein said carrier consists entirely of an elastically yielding plate.

5. A shock wave generator as claimed in claim 1, wherein said electrically conductive section comprises a foil.

6. A shock wave generator as claimed in claim 5, wherein said metal foil comprises aluminum.

7. A shock wave generator as claimed in claim 1, wherein said carrier has a plurality of electrically conductive sections attached thereto.

8. A shock wave generator as claimed in claim 1, wherein said membrane assembly and said coil define a volume therebetween, and further comprising means for evacuating said volume.

9. A shock wave generator as claimed in claim 1, wherein said perimeter of said carrier has a region of decreased thickness forming said elastically yielding region.

* * * * *